US009897524B1

(12) United States Patent
LaForest et al.

(10) Patent No.: US 9,897,524 B1
(45) Date of Patent: Feb. 20, 2018

(54) METHOD AND APPARATUS FOR MEASUREMENT OF PARTICLE CHARACTERISTICS USING LIGHT SCATTERING AND OPTICAL IMAGING

(71) Applicants: Jason LaForest, Abington, PA (US); Michael Trainer, Coopersburg, PA (US)

(72) Inventors: Jason LaForest, Abington, PA (US); Michael Trainer, Coopersburg, PA (US)

(73) Assignee: MICROTRAC INC., Montgomeryville, PA (US)

( * ) Notice: Subject to any disclaimer, the term of this patent is extended or adjusted under 35 U.S.C. 154(b) by 0 days.

(21) Appl. No.: 15/590,628

(22) Filed: May 9, 2017

Related U.S. Application Data

(60) Provisional application No. 62/333,943, filed on May 10, 2016.

(51) Int. Cl.
*G01N 15/02* (2006.01)
*G01N 27/447* (2006.01)
*G01N 15/14* (2006.01)

(52) U.S. Cl.
CPC ......... *G01N 15/0205* (2013.01); *G01N 15/14* (2013.01); *G01N 15/1463* (2013.01); *G01N 27/44721* (2013.01); *G01N 2015/1493* (2013.01)

(58) Field of Classification Search
CPC ............................... G01N 15/02; G01N 15/14
USPC ......................................................... 356/336
See application file for complete search history.

(56) References Cited

U.S. PATENT DOCUMENTS 5,056,918 A * 10/1991 Bott ................... G01N 15/0211
356/336
5,918,272 A * 6/1999 Snyder ................... B03C 1/288
210/222

* cited by examiner

*Primary Examiner* — Roy M Punnoose

(57) ABSTRACT

The present invention comprises methods and apparatus for measuring light scattering from particles and images of particles in the same sample cell utilizing two light sources.

14 Claims, 2 Drawing Sheets

METHOD AND APPARATUS FOR MEASUREMENT OF PARTICLE CHARACTERISTICS USING LIGHT SCATTERING AND OPTICAL IMAGING

CROSS-REFERENCE TO PRIOR APPICATIONS

Priority is claimed from U.S. provisional application Ser. No. 62/333,943, filed May 10, 2016.

BACKGROUND OF INVENTION

This invention relates to systems and methods for analyzing particles using light scattering from particles and imaging of particles.

SUMMARY OF INVENTION

The present invention comprises methods and apparatus for measuring light scattering from particles and images of particles in the same sample cell utilizing two light sources. A first particle size distribution is determined from said light scattering measurements; and a second particle size distribution is determined from said imaging measurements. Said first and second particle size distributions are combined into a single particle size distribution which covers a broader particle size range.

DETAILED DESCRIPTION OF THE INVENTION

Figure 1:
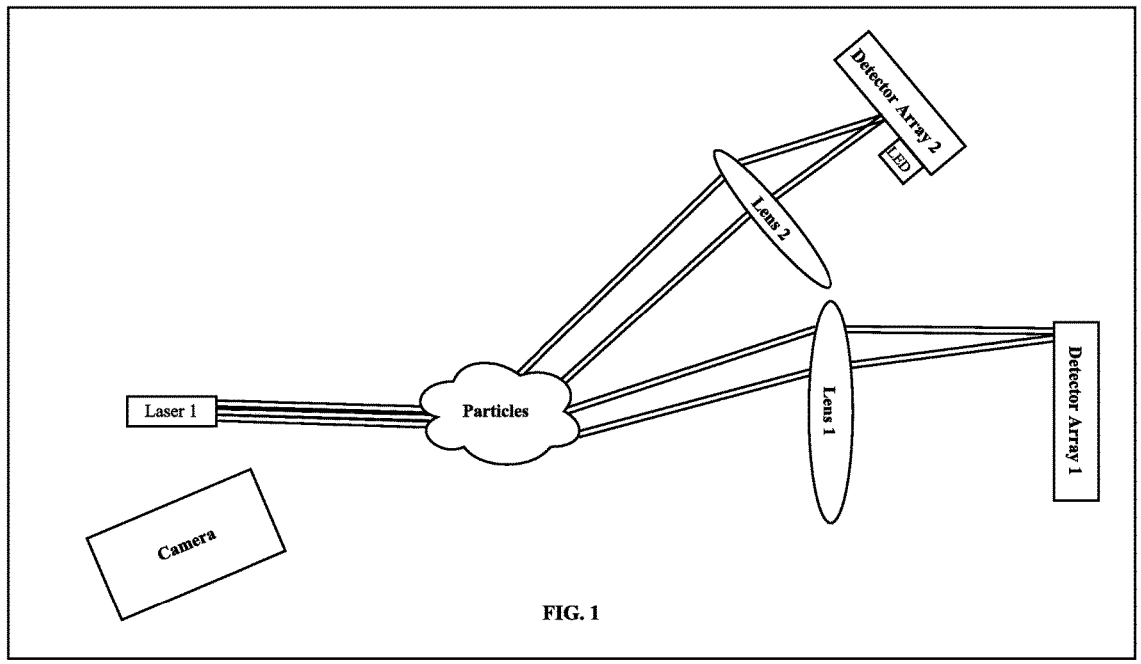
FIG. 1 describes an optical configuration for measurement of scattered light from particles.

The invention relates to the measurement of characteristics of small particles, wherein said characteristics comprise particle size distributions, including particle volume, particle area, and particle number per diameter interval. U.S. Pat. No. 5,416,580 describes an example of a static scattering method and apparatus for measuring scattered light. Diffraction or static scattering systems determine particle size distribution by analyzing the angular scattering distribution from an ensemble of particles. These scattering measurements accurately determine the size of small particles down to 10 nanometers in diameter. Large particles scatter light at very low scattering angles, where background scatter can interfere with accurate measurement of the angular scattering distribution. Therefore, large particle size measurement is difficult with scattering methods. Imaging methods provide an effective complimentary particle size measurement method to light scattering. Imaging methods measure larger particles with high accuracy. However, since the ultimate resolution of imaging is limited by diffraction of the imaging optical system, optical imaging cannot accurately measure very small particles. Therefore, the combination of optical imaging and light scattering methods and apparatus is effective for measuring accurate particle size over a large particle size range by utilizing each methodology to measure particles in the size range where that methodology provides optimum performance. Angular light scattering measurements are utilized to measure particles in the small size portion of the size range and optical imaging measures the size of particles in the large size portion of the size range. The size ranges of both methods are designed to have significant overlap in size to provide a common size region where the two size distributions are combined and scaled.

Each method measures particles which flow through the same sample cell, which comprises windows to allow optical access to particles passing through the cell. Since each method measures portions of the same generally homogeneous particle dispersion, each method will produce particle size distributions, which are representative of the same particle dispersion. This common representation is further insured by measuring many different portions of the same dispersion and averaging those results for each method. The imaging optical system and scatter measuring system each have a separate light source, which can be illuminated over specific time periods to avoid interactions between the two systems. In this way, the scattering detectors do not receive light scattered from the imaging light beam and the particle images of the imaging system do not contain imaging artifacts created by particle illumination from the scattering light source. In particular, the scattering light source is usually a coherent laser source, which produces high intensity for scattering measurements, but which would provide images with coherent light artifacts. The imaging system utilizes a generally incoherent source to avoid said coherent light artifacts. In cases where the angle between the two light source beams is large, the detected particle scattered light from the scattering light source will be negligible in the imaging detector as compared to the detected particle imaging light from the imaging light source. In these cases, the scattering light source can remain on during the imaging process.

Figure 2:
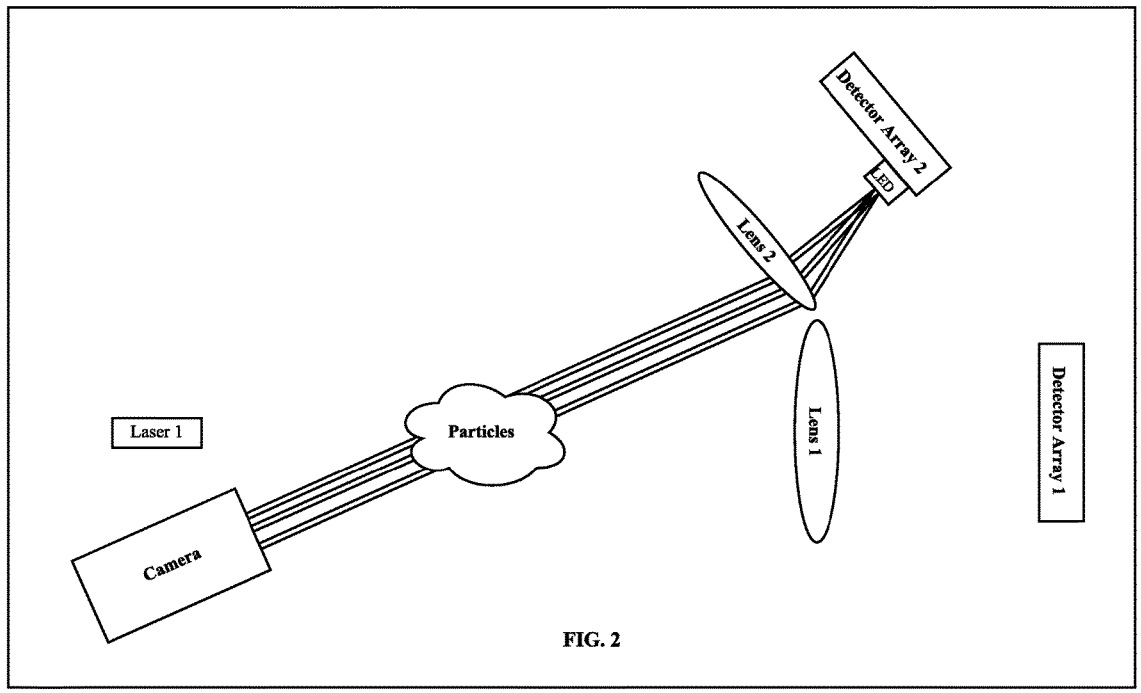
FIG. 2 describes an optical configuration for measurement of images from particles.
Figure 3:
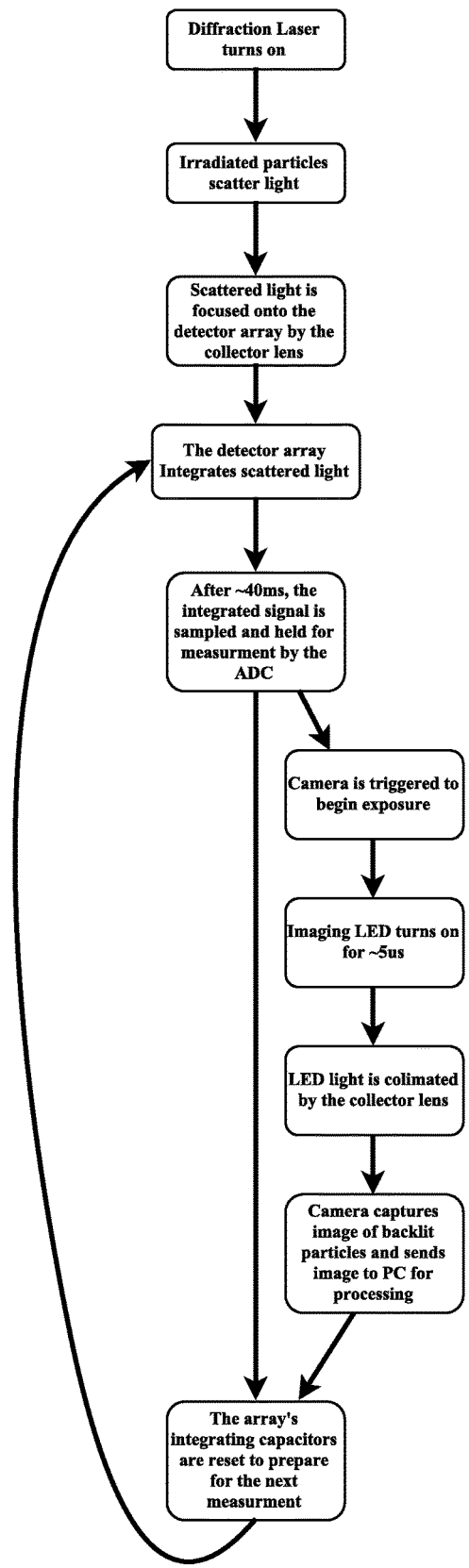
FIG. 3 describes the process flowchart of collecting scattering and imaging measurements.

During a diffraction measurement, a light source, such as a laser, irradiates particles flowing through the sample cell or sample region, as shown in FIG. 1 and as described in U.S. Pat. No. 5,416,580, for example. Light scattered from these particles is focused onto a detector array by a lens. Each detector element measures scattered light over a different range of scattering angles. After an integration period, the measured values, of the detector array, are temporarily stored by the sample and hold capacitors. While these values are being multiplexed and read by the analog to digital convertor, the arrays are reset and their integrating capacitors are drained to prepare for the next diffraction measurement. The digital values can be stored in a storage device, such as RAM memory. The array reset occurs during a short period, such as 5 milliseconds. During this reset period, the camera performs an exposure of a new image and the imaging light source, such as a LED (light emitting diode), flashes for a short period, as shown in FIG. 2. The resulting digital imaging data can be stored in a storage device, such as RAM memory. This cycle of scatter light integration/digital storage and image detection/digital storage is repeated until sufficient particles have been measured. In cases where space is limited, the light from the LED can be collimated by the same lens that focused the scattered light from the diffraction measurement, as shown by lens 2 in FIG. 2 for example. This light illuminates the sample particles from behind, allowing the camera to capture an image of the particle profiles. Because the LED only flashes while the arrays are being reset, the diffraction data is not impacted by the LED light. This allows for sequential diffraction and imaging measurements to be taken using a single sample cell. This process is also described in the process flowchart of FIG. 3.

Two particle size distributions are created from these measurements. The light scattering distribution of scattered light intensity vs. scattering angle is measured for groups of particles. This scattering distribution is then inverted by an algorithm to produce a first uncorrected particle size distribution, such as particle volume vs. particle diameter, for example. The imaging system produces images of each particle which is in the field of the imaging lens during the LED flash period. The pulse length of the LED is short to avoid elongated particle images due to particle motion during the LED illumination period. The dimensions of each particle image are measured and these measurements are sorted into different particle size ranges to produce a second uncorrected distribution of particle count vs. particle diameter. The effective particle diameter of each counted particle can also be determined from the equivalent area of each particle image, for example. Each uncorrected distribution will usually result from averaging of many measurement cycles of scatter light integration/digital storage and image detection/digital storage to accumulate sufficient data from a representative sample of the particle dispersion and to improve measurement accuracy.

Both of said first and second uncorrected distributions are converted to the same size distribution parameter, such as particle number, particle volume, or particle area per particle size interval to produce two corresponding distributions, with the same parameter. The imaging optical system and scattering measurement system are designed to have an overlapping size range, wherein the larger size portion of the first distribution and the smaller size portion of the second distribution overlap to create a common size region. Then the ratio of a sum of data points within a common size region between the two distributions is used to change the scale of one of the distributions to bring both distributions onto an equal amplitude scale, using the following procedure wherein Vu1 and Vu2 are uncorrected first and second particle size distributions, respectively, with the same distribution parameter vs. particle size interval.

$$V1(di)=Vu1(di)$$

$$V2(di)=k*Vu2(di)$$

$$k=\text{sum}(Vu1(a:b))/\text{sum}(Vu2(a:b))$$

Wherein di is particle diameter at the center of the ith particle size interval and V is the particle parameter per particle diameter interval. For the case where the distribution parameter is particle volume, V is the particle volume per particle size interval.

And k=sum(Vu1(a:b))/sum(Vu2(a:b)) where the size index range a:b defines a range in said common size region and sum(X(a:b)) is the summation of values of X(di) over range i=a to i=b. This procedure creates first distribution, V1, and second distribution, V2, from said first and second uncorrected distributions, respectively. After this scaling process, the two distributions are combined over a predetermined size overlap region, where both methods provide acceptable particle size accuracy over the same particle size region. Within this overlap region the two distributions are combined by the following equation:

first distribution from scattering measurements: V1(di)
second distribution from imaging measurements: V2(di)
d1=particle diameter at start of overlap region
d2=particle diameter at end of overlap region
Then the final distribution V(di) is given by:

$$V(di<d1)=V1(di<d1)$$

$$V(di>d2)=V2(di>d2)$$

$$V(d1<=di<=d2)=Fi*V1(di)+(1-Fi)*V2(di)$$

where Fi is a generally monotonic function such as a linear function for example:

$$Fi=(i-i1)/n;$$

where i=i1, i1+1, i1+2, . . . i1+n and i1 is the index corresponding to d1 and i1+n is the index corresponding to d2.

The final distribution, V(di), can be converted to other types of distributions by using known methods. For example, if V(di) is particle volume per particle size interval, then particle number distribution, N(di), is created by the following equation for example:

$$N(di)=6*V(di)/(pi*di^3)$$

What is claimed is:

1. An apparatus which determines a particle size distribution from scattering measurements of particles and imaging of particles comprising:
   a) a first light source which illuminates particles for detection of scattered light from particles, wherein said light source is turned on during a first period,
   b) a second light source which illuminates particles for imaging of particles, wherein said light source is turned on during a second period,
   c) at least one first detector which detects a first signal derived from light scattered from particles, wherein said first detector integrates said first signal over a first detection period,
   d) at least one second detector which detects a second signal derived from an image of particles, wherein said second detector detects said second signal over a second detection period, wherein said second detection period and said first detection period do not comprise a common period in time, and wherein said first detection period and said second period do not comprise a common period in time,
   e) means which determines a first particle size distribution from said detection of scattered light from particles,
   f) means which determines a second particle size distribution from said imaging of particles, and
   g) combining means which combines said first particle size distribution and said second particle size distribution to create a third particle size distribution with larger size range, wherein said third particle size distribution comprises three size regions which comprise a small size region, a size overlap region, and a large size region, wherein said third particle size distribution, in said small size region, comprises a portion of said first particle size distribution, wherein said third particle size distribution, in said large size region, comprises a portion of said second particle size distribution, and wherein said third particle size distribution, in said size overlap region, is derived from said first particle size distribution and said second particle size distribution.

2. The apparatus of claim 1 wherein said second detection period and said first period do not comprise a common period in time.

3. The apparatus of claim 1 wherein said second period and said second detection period occur while an integrator of said first detector is being reset, such that said first detector will not detect light originating from said second light source.

4. The apparatus of claim 1 wherein said first period and said first detection period occur while said second detector is not detecting light, such that said second detector will not detect light originating from said first light source.

5. The apparatus of claim 1, wherein said second detector is the member of a group of detectors, wherein said group comprises a detector array.

6. The apparatus of claim 1, wherein said first detector is the member of a group of detectors, wherein said group comprises a detector array.

7. The apparatus of claim 1, wherein said combining means further comprises:
   a) means which provides an overlap region of size for said first particle size distribution and said second particle size distribution,
   b) means which utilizes a generally monotonic function of particle size to combine said first particle size distribution and said second particle size distribution in said overlap region to create said third particle size distribution in said overlap region.

8. The method of claim 7 wherein said generally monotonic function comprises a linear function.

9. A method which determines a particle size distribution from scattering measurements of particles and imaging of particles comprising:
   a) providing a first light source which illuminates particles for detection of scattered light from particles, wherein said light source is turned on during a first period,
   b) providing a second light source which illuminates particles for imaging of particles, wherein said light source is turned on during a second period,
   c) providing at least one first detector which detects a first signal derived from light scattered from particles, wherein said first detector integrates said first signal over a first detection period,
   d) providing at least one second detector which detects a second signal derived from an image of particles, wherein said second detector detects said second signal over a second detection period, wherein said second detection period and said first detection period do not comprise a common period in time, and wherein said first detection period and said second period do not comprise a common period in time,
   e) determining a first particle size distribution from said detection of scattered light from particles,
   f) determining a second particle size distribution from said imaging of particles, and
   g) combining said second particle size distribution and said first particle size distribution to create a third particle size distribution with larger size range, wherein said third particle size distribution comprises three size regions which comprise a small size region, a size overlap region, and a large size region, wherein said third particle size distribution, in said small size region, comprises a portion of said first particle size distribution, wherein said third particle size distribution, in said large size region, comprises a portion of said second particle size distribution, and wherein said third particle size distribution, in said size overlap region, is derived from said first particle size distribution and said second particle size distribution.

10. The method of claim 9, wherein said second detection period and said first period do not comprise a common period in time.

11. The method of claim 9 wherein said second period and said second detection period occur while an integrator of said first detector is being reset, such that said first detector will not detect light originating from said second light source.

12. The method of claim 9 wherein said first period and said first detection period occur while said second detector is not detecting light, such that said second detector will not detect light originating from said first light source.

13. The method of claim 9 wherein step (g) further comprises:
   a) providing an overlap region of size for said first particle size distribution and said second particle size distribution,
   b) utilizing a generally monotonic function of particle size to combine said first particle size distribution and said second particle size distribution in said overlap region to create said third particle size distribution in said overlap region.

14. The method of claim 13 wherein said generally monotonic function comprises a linear function.

* * * * *